United States Patent
Jones et al.

(10) Patent No.: US 8,031,910 B2
(45) Date of Patent: Oct. 4, 2011

(54) METHOD AND APPARATUS FOR ANALYZING QUALITY TRAITS OF GRAIN OR SEED

(75) Inventors: Michael A. Jones, Ankeny, IA (US); David J. Foster, Ankeny, IA (US); Doris M. Rimathe, Madrid, IA (US)

(73) Assignee: Syngenta Participations AG, Basel (CH)

( * ) Notice: Subject to any disclaimer, the term of this patent is extended or adjusted under 35 U.S.C. 154(b) by 1342 days.

(21) Appl. No.: 10/928,760

(22) Filed: Aug. 27, 2004

(65) Prior Publication Data

US 2005/0074146 A1 Apr. 7, 2005

Related U.S. Application Data

(60) Provisional application No. 60/503,655, filed on Sep. 17, 2003.

(51) Int. Cl.
G06K 9/00 (2006.01)

(52) U.S. Cl. .......................................................... 382/110

(58) Field of Classification Search .................. 382/110, 382/141, 162; 356/72, 406, 446; 250/339.07; 209/581; 111/100, 118, 200
See application file for complete search history.

(56) References Cited

U.S. PATENT DOCUMENTS

| | | | |
|---|---|---|---|
| 3,385,434 A | 5/1968 | Nelson | |
| 3,830,289 A | 8/1974 | Olson | |
| 4,260,262 A | 4/1981 | Webster | |
| 4,734,584 A | 3/1988 | Rosenthal | |
| 4,975,863 A * | 12/1990 | Sistler et al. | 382/110 |
| 5,321,764 A * | 6/1994 | Cullen et al. | 382/110 |
| 5,480,354 A * | 1/1996 | Sadjadi | 460/7 |
| 5,779,058 A * | 7/1998 | Satake et al. | 209/581 |
| 5,808,681 A * | 9/1998 | Kitajima | 348/371 |
| 5,835,206 A | 11/1998 | Traggesser | |
| 5,917,927 A * | 6/1999 | Satake et al. | 382/110 |
| 6,002,793 A * | 12/1999 | Silver et al. | 382/152 |
| 6,402,358 B1 | 6/2002 | Larimer | |
| 6,646,264 B1 * | 11/2003 | Modiano et al. | 250/339.07 |
| 7,218,775 B2 * | 5/2007 | Kokko et al. | 382/156 |
| 2003/0048927 A1 * | 3/2003 | Sato et al. | 382/110 |
| 2003/0112440 A1 * | 6/2003 | Fukumori et al. | 356/432 |
| 2006/0055934 A1 * | 3/2006 | Sunshine et al. | 356/446 |

OTHER PUBLICATIONS

L.W. Steenhoek, M.K. Misra, C.R. Hurburgh Jr., C.J. Bern; *Implementing a Computer Vision System for Corn Kernel Damage Evaluation.* Applied Engineering in Agriculture, vol. 17(2): 235-240 (2001).

* cited by examiner

*Primary Examiner* — Duy M Dang
(74) *Attorney, Agent, or Firm* — Dana Rewoldt

(57) ABSTRACT

The present invention relates generally to an apparatus for and a method of measuring and selecting grain for use in milling, or seed for use in plant breeding. Said method is adapted to optically analyze seeds/grains to qualitatively and quantitatively characterize the seed/grain, and more particularly, to analyze the gradation of color, whiteness, and hard endosperm of the seed/grain. This method and apparatus perform color image analysis of seed/grain sample(s) to characterize multiple quality traits.

21 Claims, 12 Drawing Sheets

METHOD AND APPARATUS FOR ANALYZING QUALITY TRAITS OF GRAIN OR SEED

This application claims the priority from U.S. provisional application, 60/503,655 having a file date of Sep. 17, 2003.

FIELD OF THE INVENTION

The present invention relates generally to an apparatus for and a method of measuring and selecting grain for use in milling, or seed for use in plant breeding. Said method is adapted to optically analyze seeds/grains to qualitatively and quantitatively characterize the seed/grain, and more particularly, to analyze the gradation of color, whiteness, and hard endosperm of the seed/grain. This method and apparatus perform color image analysis of seed/grain sample(s) to characterize multiple quality traits.

BACKGROUND OF THE INVENTION

Billions of bushels of grain (corn, soybeans, wheat, sorghum) are grown each year in the United States and enter a distribution network for purchase and utilization by various consumers, including animal feeds, industrial uses and human food processing. Grain varies in its quality and physical attributes from location to location due to genetic differences, local environmental conditions, agronomic production practices and physical handling and shipping treatment. Grains from different locations are combined in large storage and shipping containers for both domestic and export use.

In order to protect the consumer and provide assurances that the product purchased meets consumer needs, the U.S. Congress enacted the United States Grain Standards Act (USGSA) (Aug. 11, 1916, ch. 313, 39 Stat. 453 (7 USC .sctn. 71 to 87, 111, 113, 241 to 273, 2209; 16 USC .sctn..sctn. 490, 683) in 1916 to provide a uniform descriptive system for long distance trading of grain. The Federal Grain Inspection Service (FGIS) was created within the U.S. Department of Agriculture (USDA) to: (1) establish uniform Grades and Standards, and (2) to implement nationwide procedures for accurate and unbiased test results. In general, the Grain Standards factors assess physical condition or biological stability of the grain and generally fall into at least one of the following categories:

Grade determining: provides a numerical Grade based on the level of the poorest of factors including test weight, heat damage, total damage, broken corn/foreign material (BCFM).
Mandatory non-grade determining: grain moisture, broken corn, and foreign material.
Class: grain color or type—yellow, white, mixed.
Special Grade designations: special situations, i.e., insect infestation, type of grain endosperm, i.e., waxy, flint.
Optional official criteria: factors requested by party requesting inspection, i.e., protein percent in wheat, which is a measure of end-use value.

(See, "Quality Corn; The United States Grades and Standards"; Iowa Corn Growers Association, January, 1990, No. 2 of 6.)

Since the inherent quality of grains is not routinely measured and included in the USGSA, end-users have set their own internal standards to assure the grain purchased for their processing needs provides the greatest efficiency and return. Such factors may include, but are not limited to, color gradation, percent protein, oil, starch and hard endosperm. These traits are of particular interest to wet and dry millers of corn.

Wet millers process grain by steeping the grain in liquid(s) of varying composition to extract the starch, protein, gluten, oil, and hulls. Starch is further processed for various industrial starch uses, or converted into sweeteners or alcohol. Protein and gluten fractions are generally sold as animal feeds.

Dry millers process grain by mechanically breaking and separating the grain fractions through a series of rollers and shakers into the various sized components. Based on size and composition, these components are referred to as grits, meal, flour, germ and bran. These fractions are purchased by end-users for processing into cereals, snack foods, baking products, brewing and other industrial uses. Larger grit particle size is of the greatest value. A variant of dry milling is alkaline-cooking which produces dry masa flour for Mexican foods such as tortillas and snack foods.

In recent years, the ability to identify, preserve, ship and distribute grains with specific traits of added value to the seedsman, the grower, and the end-user, has increased interest in a systematic means of consistently characterizing grain for those specific traits of interest. Further, plant breeders need quick, accurate, reliable analysis methods on which to base individual plant selections in their breeding schemes. The specific traits of particular interest to millers vary from mill to mill depending upon the milling process and the type of product manufactured by the end-user. In general, for wet milling, if grain is US Grade No. 2 or 3, no other additional requirements exist for acceptance. There are some exceptions, such as wet mills that require highly extractable starch, or starch with unique cooking attributes.

In dry milling and alkaline cooking, where food products are manufactured, a host of grain characteristics may be evaluated to determine which hybrids produce grain which best meet the specific needs. In general, color gradation and hardness are two grain characteristics of particular interest because of consumer preference in the appearance and texture of the food. Grain color has a direct impact on product color, especially in alkaline cooking. Hardness affects ease of milling as well as product texture and yield, and is essentially a function of the relative proportion of vitreous (hard) to floury (soft) endosperm in the grain. Some grain cooking characteristics, such as pericarp removal, are also critical in the manufacture of food products, but these traits cannot be evaluated without expensive milling/cooking trials (actual or simulated), and therefore are not measured by millers until the final stages of hybrid selection.

White corn processors prefer a "clean" white color, without tones of yellow, red or a "dirty" (i.e., gray) cast. Yellow food corn processors prefer a "bright, medium-yellow" color. As the descriptions suggest, color ratings are highly subjective. Some analyses attempt to compare grain to a standard color chart, e.g., Hunter Color Scale, to evaluate grain (see, "Intrinsic Value of Nebraska Corn: 1994 Crop Year Report"; Jackson, Nebr. Corn Board, P.O. Box 95107, 301 Centennial Mall South, Lincoln, Nebr. 68509-5107); but more often ratings over a scale of 1-5 are given based on the expertise of the observer. Ratings of 4-5 are too dark, and 1-2 may be too light or pale in color. Grain with unacceptable color results in products that have unsatisfactory consumer acceptance. To date, the color analysis of seeds and grain for milling purposes is still commonly based upon subjective ratings.

Quantitative characteristics of grain seed including protein, oil and starch content as well as methods of qualitatively distinguishing between seed types have been available for some time. Some examples of such methods are described in U.S. Pat. No. 3,385,434 to Nelson, U.S. Pat. No. 3,830,289 to Gray, U.S. Pat. No. 4,260,262 to Webster and U.S. Pat. No. 4,734,584 to Rosenthal.

Nelson teaches a method of sorting seed corn from field corn based on the transluminescent characteristics of each. The apparatus described by Nelson contains a strong light beamed from multiple directions against the kernels of corn in a manner that allows for detection and comparison of reflected and transluminescent light. Nelson then sorts the kernels according to their transluminescent characteristics while ignoring the surface reflected light.

Gray teaches that Nelson's method is relatively unreliable in practice because of the unpredicted effects of reflected radiation and because of the size difference of the seed corn kernels. Gray provides a sorting method based on measuring and comparing the shadow pattern of at least two areas of light attenuation through a seed. Neither Gray nor Nelson teach the existence of a correlation between hard endosperm percent and the amount of transmitted light or a manner of calculating same.

Webster describes the use of photo-optical grain quality analyzers that calculates seed characteristics, such as oil percentage, water percentage, and protein percentage, from measurement of reflected infrared light.

Rosenthal provides an apparatus for near infrared illumination of seeds and detection of reflected light from same for calculation of seed characteristics.

See also the Abstract of a presentation by M. R. Paulsen, (Machine Vision for Corn Inspection, Abstract of presentation at the 1992 Grain Quality Conference in Champaign, Ill., Mar. 17, 1992) wherein is disclosed a machine vision system containing an image processing board, a microcomputer with monitor, a display monitor, a solid state CCD camera, and a lighting chamber for holding samples. Paulsen describes the following four applications for his system which include measurement of kernel length, detection of stress cracks in kernels, detection of cracks in the pericarp with the use of dye staining and distinguishing between whole and broken kernels. Paulsen states that development of his system is continuing in an effort to detect corn color and kernel hardness. The Abstract does not include a detailed description of how to repeat Paulsen's work or detailed results of the accuracy or reliability of the methods employed.

One of skill in the art will appreciate that a corn kernel consists of a germ (embryo) and endosperm covered by a seed coat or pericarp. The germ is the major oil source within the kernels and accounts for about 11% of the kernel. Approximately 83% of the kernel consists of endosperm with a composition mostly of starch but also protein and other constituents. The pericarp (bran) accounts for another 5%, and the tip cap constitutes the remaining 1% of the kernel. The makeup of the endosperm determines the processing usage of the grain. Endosperm consists of varying percentages of soft and hard endosperm. Generally, soft endosperm grains are preferred by wet millers and hard endosperm grains are preferred in dry milling and alkaline cooking. Starch is typically more easily extracted from soft endosperm grain types. Kernels with a high proportion of hard endosperm are less likely to break during shipping, will produce a high dry milling yield of large more valuable grit components, and in the alkaline cooking process are less likely to be overcooked or damaged. There is an optimum hardness for alkaline cooking, however, and hybrids with very hard (flinty) grain are undesirable because they require too long to cook.

Numerous ways of estimating grain hardness have been employed over the years. Hardness, as the ratio of hard/soft endosperm, has been quantified directly with time-consuming measurements on dissected kernels, and has also been estimated with subjective ratings. Another aspect of hardness, the resistance to crushing or breaking, has been approximated using various physical devices designed to simulate milling processes or grain handling stresses. Hardness has also been estimated in an indirect way by measuring grain density (weight per unit volume), which is a highly correlated trait. Measurements of both density and resistance to breakage are influenced by grain moisture content, and require either that all samples be of similar moisture or that a correction factor be used.

Visual observation of grain over a light box, followed by a subjective rating given by an experienced person, has long been a common screening method for grain hardness. Soft endosperm is more opaque and does not transmit much light, while hard endosperm is more translucent and transmits more light. Although an important benefit of this method is time efficiency, such ratings depend on the "eye of the beholder" and vary based on the person rating the grain, so that hybrids producing acceptable grain for one processor may not be acceptable to another. In a breeding program to improve grain texture of the plant's seed or of the final grain, high data variability often occurs due to multiple raters. To counteract this a single person bears the burden of observing and rating thousands of samples to minimize such variation. Even then, variation occurs due to fatigue and observer errors.

A convenient and commonly accepted method of estimating hardness in the grain industry is the measurement of test weight, a density-based assessment. Actually, test weight is not a measure of true density but bulk density, and is obtained by weighing a given volume of grain and making an adjustment for moisture. Test weight is widely used as a quick test for quality (and grade determination) of commodity grains at points of sale, in breeding yield trials, and even in the approval of grain for wet milling applications. Test weight has also been shown in some instances to be positively correlated with dry milling yield and is used by some food grade end-users. It is known, however, that test weight data can be misleading due to the confounding of other grain characteristics such as kernel shape, and therefore it's value is limited.

Another conventional and commonly performed test is the "floaters" test. Although this test purports to provide an indirect measure of kernel hardness, it is actually more a measure of the uniformity of the grain in regard to density. In this test, the number of kernels which float in a 1.275 specific gravity solution are counted, and relative hardness is read from a chart which accounts for grain moisture. Processors generally specify a maximum percent floaters allowable. This is a fairly time consuming process of counting a given number of kernels per sample, involving placing the kernels in the solution, counting and removing same from the solution.

Another commonly used device for evaluating density is the pycnometer, which depends upon the displacement of gas. A weighed grain sample of optimum moisture is placed in a sealed chamber followed by pressurized gas, such as nitrogen, which displaces the atmospheric air in the chamber. The amount of gas entering the chamber is related to hardness, and is a function of grain porosity, endosperm texture, as well as inter-seed space.

Scientists and end-users have also attempted to quantify hardness based upon resistance to physical damage. A hardness index developed using a tangential abrasive dehulling device (TADD) was used in a 1995 Texas Foodcorn Performance Test, as described by Bockholt et al. (1995 Texas Food Corn Performance Test; The Texas Agricultural Experiment, Station/Department of Soil & Crop Sciences, Texas A&M University, College Station, Texas). In that test, the amount of material removed, expressed as a percentage of the total sample, is related to the relative proportions of hard to soft endosperm, kernel size and shape, and type of denting. It requires 45 gm of whole kernels and is a destructive technique. Seeds cannot be later used for any purpose, which is a major drawback in a breeding program, where it is desirable to select and plant the best kernels.

Near-infrared reflectance (NIR) and near-infrared transmittance (NIT) analyzers are becoming increasingly popular for quick estimation of numerous grain traits including moisture, extractable starch, test weight, and kernel density. Grain samples are irradiated with light of varying wavelengths over a range from about 400 to 2,500 nm. Electronic detectors measure the absorbance of light by the grain at the different wavelengths. The pattern of absorption is a function of the type and concentration of chemical bonds in molecules within the grain. Statistical programs are available to solve the complicated calibrations which link the absorption patterns to actual grain properties measured with standard procedures. NIR and NIT analyzers offer some advantages because they are rapid and non-destructive. The reliability of the results depends upon the quality of the calibrations, and precision can only approach but never equal that of measurements obtained directly with actual procedures.

More recently, a method and apparatus disclosed in U.S. Pat. No. 5,835,206 to Tragesser, the entire disclosure of which is hereby incorporated herein by reference, describes the use of a color image analyzer for quantifying seed/grain quality traits. The main benefit of Tragesser's disclosed method and apparatus is a fairly quick and subjective estimate of grain hardness, through the calculation of hard endosperm area as a percent of total kernel area. With Tragesser's apparatus, a color video camera and a computer are used to capture and analyze white light that is passed through a back-lit seed/grain sample. FIG. 1 shows an example of Tragesser's apparatus. As illustrated, light is directed through a first linear polarizing light filter (25) and then through the seed sample (10). Light transmitted through the seed sample is collected by a video camera (15) after having passed through a second linear polarizing light filter (7) that is oriented with its direction of polarization orthogonal to that of the first polarizing filter (25). The use of cross polarizing filters in this manner prevents extraneous background/ambient light that does not pass through the seed/grain sample from interfering with the analysis of light passing through the sample. Pixel intensity and color data are acquired from the camera and analyzed, using conventional software, to quantify certain grain traits such as hard endosperm percent, kernel area, hue (gradation of color), saturation (whiteness), and intensity. Since the quantification of grain hue and saturation is based on whole kernel images, it is influenced by embryo color and size, as well as grain texture. For certain end-users, the estimations of grain hue and saturation using this method can be occasionally inappropriate because unused portions of the kernel (embryo, soft endosperm) can influence the results.

There remains a need for a convenient and accurate method and apparatus for evaluating important quality indicative characteristics of seeds/grains such as, for example, grain color. There remains a need for a method and apparatus employing non-polarized visible light. There furthermore remains a need for a method and apparatus that does not employ near-infrared reflectance (NIR) or near-infrared transmittance (NIT) analyzers, or external polarizers but instead uses direct visual range light.

SUMMARY OF THE INVENTION

The present invention provides a method and apparatus for performing optical analysis of seeds/grains, based on color gradation and hard endosperm percentage to obtain an objective determination of seed/grain quality and for solving, or at least diminishing, the above discussed problems associated with the other conventional approaches.

Broadly then, the present invention includes the method of optically analyzing seed and/or grain quality. This method has steps comprising: acquiring an image of an illuminated area of a stage containing a seed/grain sample, the image comprising a plurality of pixels wherein each pixel has at least an associated Red (R), Green (G) and Blue (B) color value. Identifying a subset of pixels in the image that correspond to seed/grain areas of the image. These are called grain pixels. Identifying another subset of pixels that correspond to hard endosperm portions of the seed/grain sample. These are called hard endosperm pixels. Analyzing pixels to assert the seed/grain quality. The method can be employed to determine a value indicative of a percentage of pixels identified as grain pixels that also correspond to the hard endosperm pixels.

This method envisages a first light source positioned to project light through the stage which supports the sample. This first light being of sufficient intensity such that at least some light passes through both the stage and the sample, and with this first light the plurality of pixels and the grain pixels or the hard endosperm pixels are acquired. The stage supporting the sample is translucent or transparent so that the light can transmit through the stage.

The first light source in the apparatus for examining the sample is positioned to project light such that the sample is backlit. A camera is positioned to capture light from the first light source after it has passed through the stage and the sample. This results in the capture of the backlit image. The backlit image is useful for determining kernel size and hard endosperm portion of the sample.

Additionally, if color traits such as hue, saturation and intensity are desired, a second light source can be positioned to project light wherein the sample is also frontlit.

The method allows for a stage with a first surface and an opposite second surface, so the light from a second light source initially projects through the second surface of the stage, and the light from the first light source initially projects through the first surface of the stage, resulting in a sample that is both backlit and frontlit. The camera is positioned to capture light transmitted through the sample and stage from the first light source, and light from the second light source that is reflected from the sample. This front/backlit image can be employed in determining color traits of the sample by computing one or more of average hue, average saturation or average intensity of just the hard endosperm pixels. Color trait estimates from the hard endosperm pixels are more useful to some end-users than estimates based on all of the grain pixels, because the hard endosperm portion of the grain has a more direct bearing on the final product color.

The method of the present invention can have a pixel R, G, B color value corresponding to a predetermined white color. A pixel from the plurality of pixels of the image is identified as a pixel within the subset of pixels corresponding to grain pixels if the pixel has R, G and B color values that are not equivalent to a white color. In some embodiments the predetermined pixel RGB color value respectively consists of R, G and B color values of: R=255, G=255 and B=255. The R, G, and B values depend on the number of total pixels in a set area that are analyzed. Thus this value will depend upon the computer program's pixel parameters. The ordinarily skilled person in the art can determine the white value of R, G, and B readily. Additionally, the method can identify pixels corresponding to hard endosperm pixels as pixels having an intensity value that is greater-than or equal-to an average grain pixel intensity multiplied by a predetermined equipment adjustment factor.

In another embodiment of the invention is a method of breeding corn comprising the steps of analyzing corn seed for the desired traits with the apparatus and selecting corn seed with at least one desirable quality comprising hard endosperm area, hard endosperm percent, hue, or saturation;

Once the seed or seeds are selected they can be grown into plants. These plants can then be bred to produce progeny seeds. The progeny seeds are also analyzed for at least one desirable quality trait, and the best seeds are selected. These selection and breeding steps can be repeated. The breeding techniques can be any used by those in the art, for example the breeding could be either inbreeding (selfing) or crossing.

The present invention also includes an apparatus for optically analyzing a seed and/or grain sample, comprising a stage having at least one surface, used for supporting a seed/grain sample, which is at least partially translucent.

The apparatus has a light source positioned proximate the stage, providing light of sufficient intensity such that at least some light also passes through the sample. And the apparatus has a camera adapted to capture an image of the sample, with a computer engaged with the camera adapted to analyze the captured image.

In another embodiment of the invention, an imaging apparatus for performing optical analysis comprises a light-table for supporting and backlighting a seed/grain sample, a camera connected to a conventional computer device, a second high intensity light source for separately illuminating the sample from above and a light-tight enclosure for eliminating all background ambient light that is not generated by the apparatus. The light-table has a translucent top support surface and houses one or more high intensity light sources for backlighting the sample. When a seed/grain sample on the light-table is backlighted, the camera is used to capture light transmittance information from the sample for identifying areas of hard and soft endosperm. By also capturing a separate image using the second high intensity light source and illuminating the sample from above, the present invention is able to obtain very accurate pixel color values for determining image hue, saturation and intensity (brightness).

In these embodiments, the hard endosperm percentage of a sample is determined from an image acquired using only a backlight (i.e., a light transmission image). A separate front-lit and backlit image of the seed/grain sample (i.e., an image obtained using illumination originating from above and below the sample) is also acquired and used for identifying hard endosperm color attributes.

In the embodiment of the invention, a method of analyzing image pixel data compensates for inconsistencies in pixel intensity ranges across an acquired image, due to such things as variability in the illumination of the stage can be employed. This optional step effectively operates as a tare for light variability, serving to remove the variability in the image analysis.

BRIEF DESCRIPTION OF THE DRAWINGS

These and other features and advantages of the present invention will be better appreciated by reading the following detailed description of an example embodiment of the invention taken in conjunction with the accompanying drawings of which.

DETAILED DESCRIPTION OF EXAMPLE EMBODIMENT OF THE INVENTION

The present invention provides a method of and apparatus for color image analysis for characterizing multiple grain quality traits in a quantitative manner. The method and apparatus of the present invention provides an arrangement for objectively determining seed/grain quality by detecting and analyzing visible light reflecting from and/or transmitted through at least one seed/grain.

Figure 1:
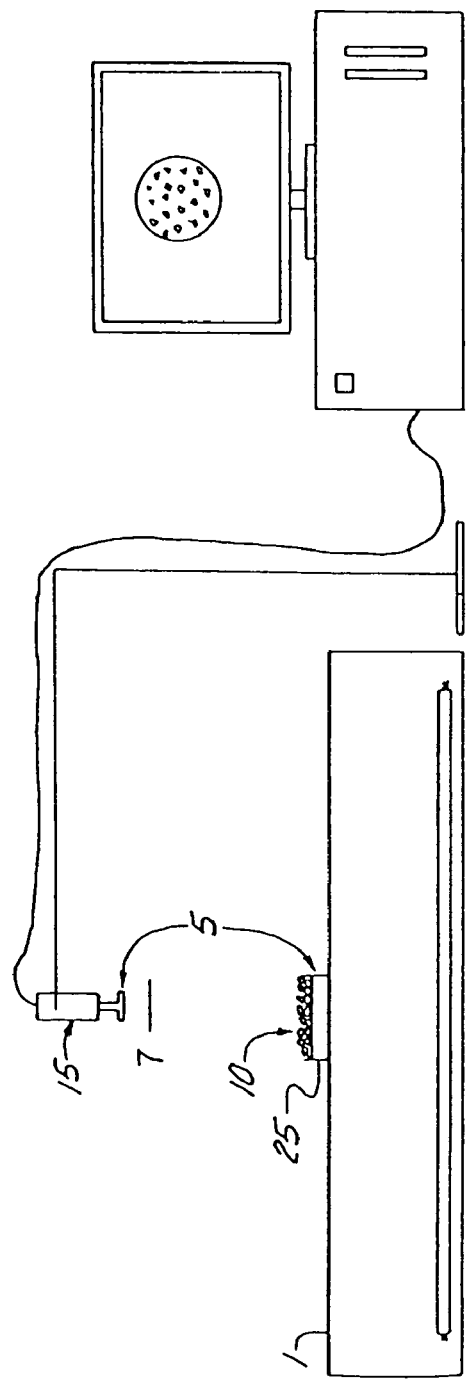
FIG. 1 is a schematic illustration of an example Prior Art apparatus for conducting optical analysis of seed/grain quality characteristics.

The Prior Art shown in FIG. 1 uses an apparatus with illumination which projects visible light toward the sample on a stage to form a back lit sample. Prior to reaching the sample the light passes through a linear polarizing light filter. The light transmitted through the filter, sample, and the stage is then transmitted through a second cross-polarizing light filter prior to being captured by the video camera. The light received by the camera is transmitted to a computer and analyzed to determine percent hard endosperm and grain color.

The present invention is somewhat similar to the Prior Art in FIG. 1 in that, when analyzing hard endosperm, the present invention employs visible light (though preferably not from a fluorescent lamp) transmitted through the sample to form a back lit sample. However, that is where the similarity ends. The Prior Art invention employs polarizing filters, but the present invention has developed a different means for precisely determining the hard endosperm percent without the use of polarizing filters or polarized light. Additionally, the present invention employs both back light and top light to illuminate the sample of seed/grain for the estimation of color traits. The use of top light to produce reflective light from the kernels in the sample with back light to produce transmitted light through the kernels in the sample, provides estimates of color traits indicative of not only the color of the external layers of the seed/grain, but also the color of the internal endosperm as well.

In all embodiments of the present invention, the method employs detection of transmitted or reflected visible light is defined as being light that comes from wavelengths within the visible portion of the electromagnetic spectrum using at least one camera (multiple cameras could be used), and the quality of the seed/grain sample is estimated with an analysis of the pixels to quantify the percentage of hard endosperm and/or color, as expressed in terms of hue, saturation and intensity. In addition, by using a standard number of kernels per sample, the average kernel size can be calculated. Furthermore, among samples of uniform kernel count, the area of hard endosperm can be used to predict dry milling yield of large grit components.

The method and apparatus of the present invention is particularly suitable for performing qualitative analysis of corn seed/grain, although seeds/grains of other crops may be qualitatively analyzed as well. For example, the present invention works particularly well for seed/grain types that have good visible light transparency of the hard endosperm but poor light transparency of the remainder of the kernel. Dicots seeds/grain such as peanut, sunflower, soybean, cotton, and canola and monocot seed/grains such as wheat, rye, oats, sorghum, barley and rice all could be employed without undue experimentation.

Figure 4:
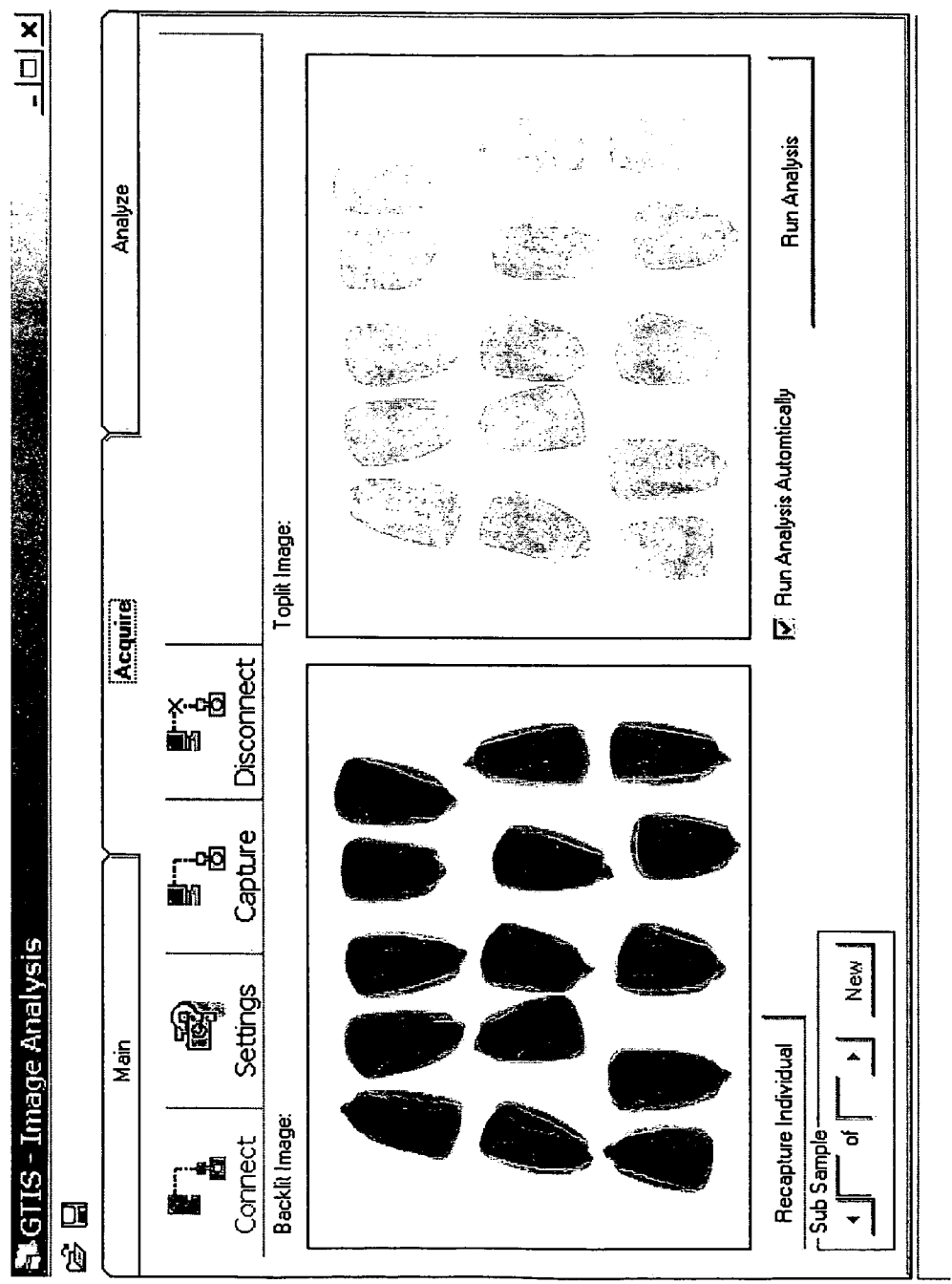
FIG. 4 is an example of computer graphics for acquiring the back-lit and top-lit/backlit images of a corn seed/grain sample produced in accordance with the present invention.

Referring to the illustration of FIG. 2, an embodiment of the method and apparatus (200) of the present invention for performing the quantitative and qualitative analysis of a sample (210) of seeds/grain is discussed below. Images of at least one kernel of seed/grain (205) are acquired by using an image-capturing device such as a camera (220). A high quality digital camera with good resolution works well (e.g. the Nikon D100 with a 60 mm lens). The embodiment shown in FIG. 2 which produced the computer analysis of the sample (210) that is shown in FIG. 4 used the Nikon D100 with the following selected settings: lens-60 mm f/2.8D AF, raw image size-small (1504*1000), shutter speed-1/100, camera lens aperature-11.0, white balance-sunny. These parameters will differ according to camera and are easily determined by adjusting with a known standard as the sample.

The camera (220) is connected to the light source (250) which provides both modeling light to show the stage and a flash. The camera (220) triggers a flash of light when an image is to be captured and sends the image data to a conventional computing device (240) such as, for example, a desktop computer, a laptop, or other portable computing device. The digital camera (220) provides digital image data to the computer (240) for constructing images comprised of a plurality of pixels, each pixel having at least an associated RGB (red, green and blue) color intensity value. Alternatively, the digital camera (220) could simply write captured image data to a portable memory storage medium for subsequent reading and processing of the image data by a remote computing device not connected to the camera. Conventional video/image capturing software and digital camera-computer interfacing hardware is used to capture, store and display acquired images and may also be used to modify the pixel data comprising the images. Image processing software applications for digital cameras and camera-computer interfacing hardware are known in the art and are readily available from common commercial vendors of computer equipment and accessories.

Figure 2:
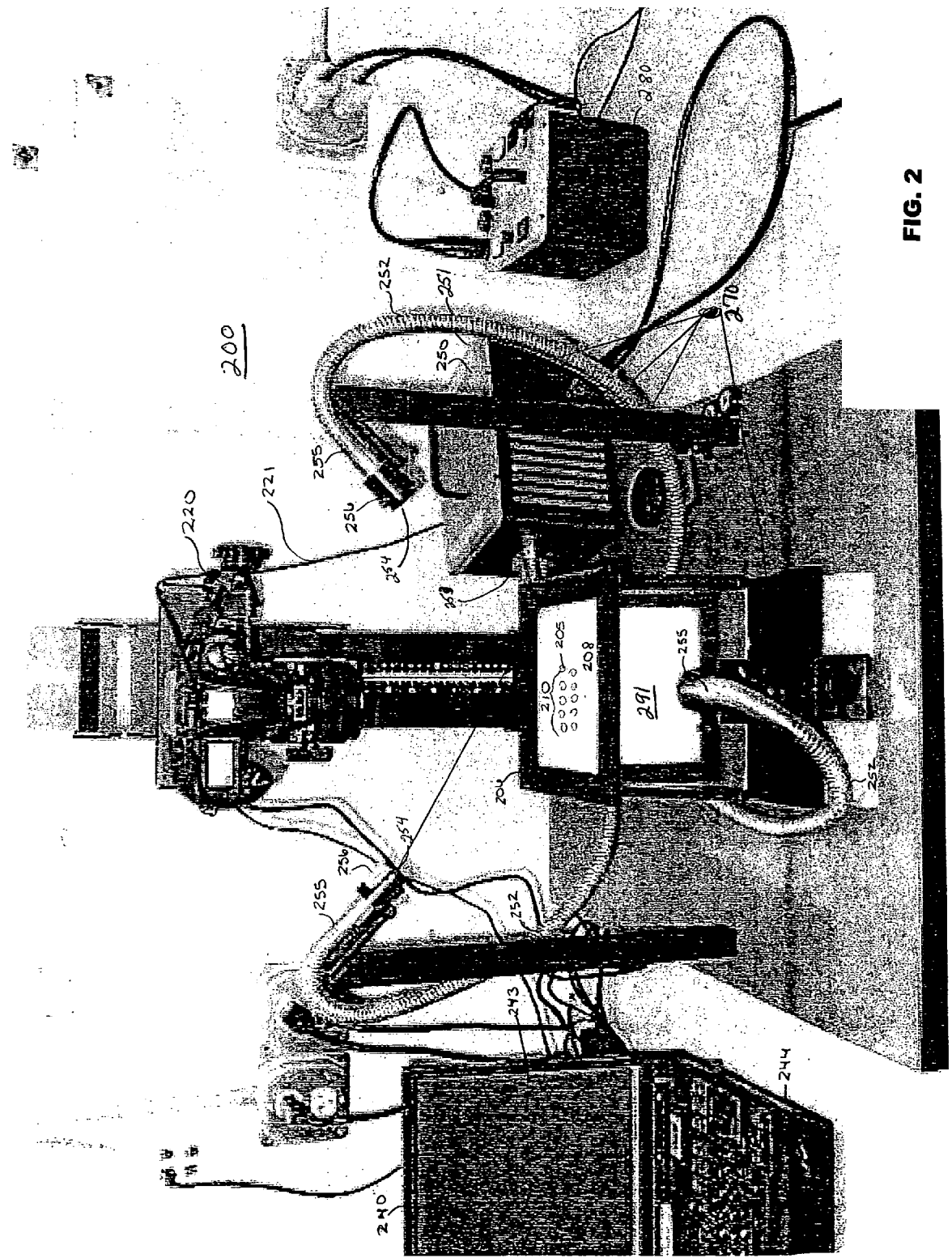
FIG. 2 is a schematic illustration of an apparatus for conducting optical analysis of seed/grain quality characteristics in accordance with the preferred embodiment of the present invention.

As illustrated in the example embodiment of FIG. 2, digital camera device (200) is shown connected to a conventional desktop computer device/system (240) having associated image display device (243) and keyboard/input devices (244). Computer display device (243) is used to display images of the seed/grain sample (210) captured via camera (220) and may display images related to data and/or other information computed by computer (240). A seed/grain sample (210) is placed upon a stage (206) (e.g. a translucent support surface (208)) that is illuminated from above and/or below using high-intensity white light source (250). Unlike the fluorescent light source taught in the Prior Art of FIG. 1, the preferred embodiment shown in FIG. 2 of the present invention employs a modeling halogen light that is a steady light and a Xenon flash when the camera triggers the light source (250). Neither the flash nor the steady light presents a flicker known to be an effect of fluorescent lighting. This flicker can cause unreliable and inconsistent results, especially in combination with digital imagery.

In FIG. 2 is shown the capacitor-discharge power supply (280), lamp housing (251) within it is the light source (250), and conduit containing fiber-optic illuminators (255) having a light receiving end (253) proximate the light source and a light projecting end (254) proximate the mechanical aperture (256) that transfer visible Xenon light from the light source (250) to the stage (206). In this preferred embodiment, the light source employs Xenon lamps to generate daylight-balanced light (with white color temperature of 5800° K), and as a result yield a very natural rendering of seed/grain color. The power supply (280), light source (250), and fiber-optic illuminators (255) are components of an illumination system (270) commercially available from Microptics, Inc. (Ashland, Va. 23005). The Microptics lighting system is described in U.S. Pat. No. 6,402,358, which is incorporated by reference in its totality. This lighting system (270) was designed to provide a consistent and very brief but intense flash of visible light, in synchrony with the camera's exposure. The camera triggers the flash of the lighting system (270) through connection (221) which links the camera (220) to the source (250). The intensity of the flash is so bright that it cancels the effect of any contaminating ambient light, reducing the need to use a darkroom or light-tight enclosure (609) such as provided in the embodiment of FIG. 6.

In FIG. 2 the projection of light onto the stage (206) can be aimed and controlled precisely through fiber optic conduits (252), each equipped with a mechanical aperture (256) for adjusting intensity. When the backlit image is needed, the mechanical apertures (256) on the fiber optic conduits (252) used for the front lighting of the sample are closed. When front/backlit image is needed, all apertures (256) are opened. The front two lights' mechanical apertures (256) are opened at a setting of 6 mm, and the bottom light's mechanical aperture (256) is at the full open setting of 11 mm. In the embodiment of FIG. 2, two fiber optic illuminators are set above the stage at 45 degree angles with the light projecting end (254) at about 220 mm from the stage center. A third illuminator is directed horizontally into a mirror, set at a 45 degree angle below the stage, with an effective distance of 220 mm from this illuminator's light projecting end (254) to the bottom of the stage. The light source in the light housing generates flashes of light with a pre-determined intensity as controlled by a variator on the capacitor-discharge power supply (280). Stage/table (206) may be constructed of a translucent or semi-transparent material (208) that provides a substantially uniform transmission and distribution of visible light from illumination source over at least the entire area in which a seed/grain sample (210) is placed. The present invention includes light sources which can be positioned in various locations to provide uniform distribution of light across the sample in both backlit and frontlit situations.

Figure 3:
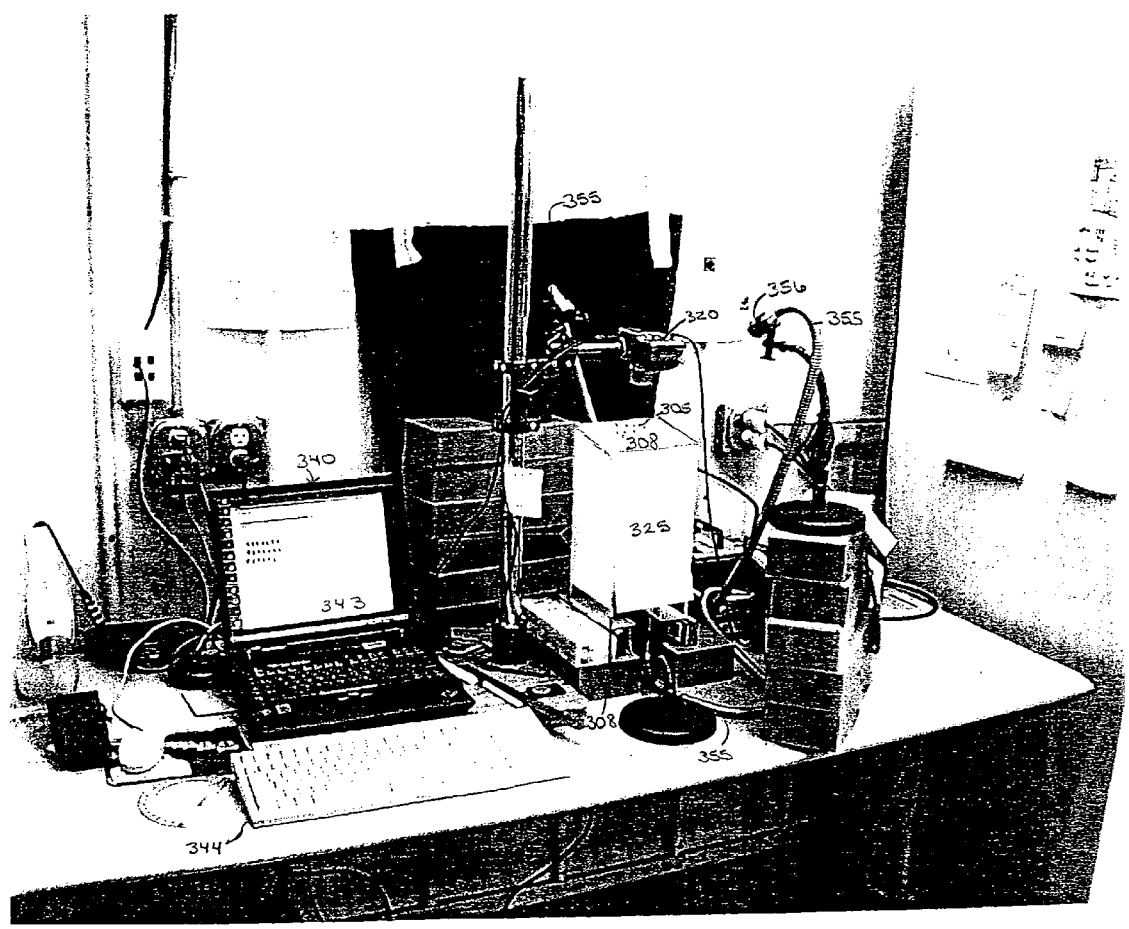
FIG. 3 is a picture of another embodiment of the invention.

In FIG. 3, the placement of the three fiber optic conduits differs from that shown in FIG. 2. In FIG. 3 the top lighting or front lighting conduits (355) are not directly across from each other as is shown in FIG. 2; however, this placement of the lighting conduits (355) still achieves a uniform distribution of light across the whole stage (308) in both bottom-lit and top-lit situations. Additionally, in FIG. 3 the light projecting portion of the backlighting conduit (355) is positioned directly beneath the stage (308) in a substantially vertical position to project light upwards toward the lower surface of the stage (308). In this FIG. 3, the stage (308) has a lower portion (325) that has light diffusing properties that assist in funneling the light toward the lower surface of the stage (308). In contrast, in FIG. 2, the light projecting portion of the backlighting conduit (255) is positioned horizontally and substantially parallel with the stage (210). In FIG. 2, the light is funneled to the lower surface of the stage (208) by projecting the light into a high quality mirror (291); and, the mirror reflects the light directly upwards into the lower surface of the stage (208), without the use of light diffusing properties in a lower portion of the stage shown in FIG. 3.

Figure 6:
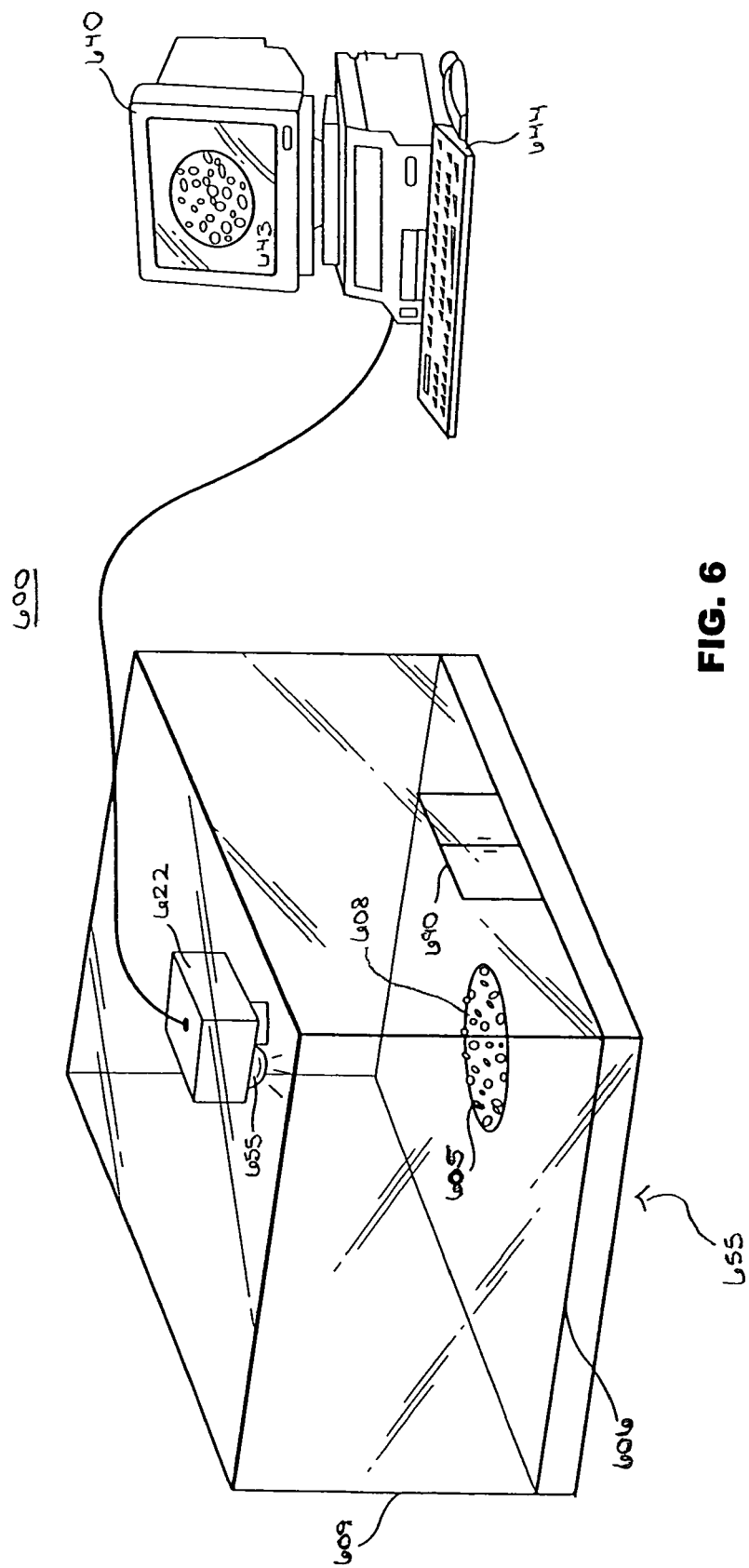
FIG. 6 is a picture of yet another embodiment of the invention.

Alternative illumination sources may also include high intensity white light sources, such as professional photography flashes, which minimize light intensity variations across the image area. This type of light source may require a light-tight enclosure (609) such as is shown in FIG. 6. The enclosure in FIG. 6 encompasses the camera (622), stage (608) and lighting components, i.e. bottom light (655) and upper light (655), to eliminate any extrinsic background/ambient light from being captured during the image acquisition process. The enclosure (609) may be provided with doors (690) or some other suitable access means for placing and/or retrieving a sample on stage/table (608). This light-tight enclosure (609) can be employed in all of the embodiments but is not particularly useful when the Microptics light source is employed. The positioning of light sources and the number of light sources can readily be altered to provide uniform coverage of the sample without undue experimentation.

In the example embodiment of the present invention, as illustrated by FIG. 2 and FIG. 3, imaging apparatus (200) and computer system are used to perform multiple operations for optically analyzing a given seed/grain sample, such as:

- Acquiring an image of the seed/grain sample on the examination stage illuminated only from behind/below (i.e., back-lit only).
- Identifying pixels in the back-lit image that correspond to seed/grain kernel areas in the image (i.e., pixels having RGB values other than predetermined white).
- Identifying and determining the percentage of pixels corresponding to the hard endosperm portions of the back-lit seed/grain image.
- Acquiring an image of the seed/grain sample on the examination stage illuminated using a pre-determined balance of back-lighting and top-lighting.
- Removing pixels corresponding to soft endosperm and embryo portions from the acquired image of the top-lit sample (i.e., removing all pixels not identified as corresponding to the hard endosperm portions in the back-lit image).
- Determining color traits from the image of the seed/grain sample, using a combination of top and bottom light, by computing average hue, saturation and intensity values for pixels corresponding only to hard endosperm portions of the image.

In the event that a light source is used that causes variation in the registered intensity values, the ordinarily skilled person could eliminate the background variation by adjusting each pixel in a calibration image to a "white" value (i.e. in this example, RGB=(255, 255, 255) and then determining a unique adjustment value that represents the percent change needed to the red, green, and blue (RGB) values of each pixel to obtain this white value for every pixel in the calibration image. These RGB adjustment values are then applied to each corresponding pixel of a captured back-lit image of a given seed/grain sample. After performing these color balancing pixel calibration adjustments to the pixels of the back-lit image of the sample, all pixels that correspond to the seed/grain kernel portions of the image will be pixels with an RGB value not equal to predetermined white. If a good uniform light source is employed this color balancing pixel calibration is rendered unnecessary and only a predetermined white value is employed.

In the present invention, pixel average hue, average saturation, and average intensity, are computed from both an acquired back-lit image and top/bottom combined image of the same seed/grain sample. A conventional computer device/system, as for example computer (240) FIG. 2, may be programmed to compute average hue, saturation and intensity values using pixel data from the captured images of a particular seed/grain sample. In an example embodiment of the present invention, computer (240) is used for such purposes and is also programmed to compute, display and/or print useful information/data about an acquired image such as one or more of at least the following:

- Total number of pixels in an acquired image
- Number/percent area of pixels identified as seed/grain kernel in an image
- Number/percent area of pixels identified as hard endosperm in an image
- Percentage pixels identified as hard endosperm across an image
- Average Hue across entire image (top/bottom combined image)
- Average Saturation across entire image (top/bottom combined image)
- Average Intensity across entire image (top/bottom combined image)

One of ordinary computer programming skill will appreciate that computer (240) may be programmed using conventional programming techniques to perform the pixel color balancing adjustments described below. This step is an optional step. For example, to make the above color balancing pixel calibration adjustments, computer (240) may be programmed to perform the following:

- For every pixel in an acquired image of an empty back-lit stage (calibration image), adjust the RGB color value to predetermined "white" value for example RGB=(255, 255, 255)) and store the percent change in each red, green, and blue color value for each pixel;
- For every corresponding pixel on the back-lit seed/grain sample image, apply the respective percent changes in RGB color values.

The following is an example for one pixel:

- Assume pixel [0,0] of the calibration image has RGB=(254, 252, 251)
- Change pixel [0,0] RGB value to RGB=(255, 255, 255) and record the percent change:
  - Red: 254 to 255=1/256=0.0039 (0.39%)
  - Green: 252 to 255=3/256=0.012 (01.2%)
  - Blue: 251 to 255=4/256=0.016 (1.6%)
- Assume pixel [0,0] on back-lit image has RGB=(180, 150, 96)
- Apply percent change adjustment values derived from calibration image to the back-lit image:
  - Red=180+(180*0.0039)=181
  - Green=150+(150*0.012)=152
  - Blue=96+(96*0.016)=98
- Use new calibration adjusted value RGB=(181, 152, 98) for pixel [0,0] of back-lit image The computer (240) is programmed to perform the following example image masking operations for identifying pixels that correspond to kernel portions of the back-lit image:

Loop through each pixel on the back-lit image and apply the following logic:
If the pixel has the predetermined white color for the RGB, in this example RGB=(255, 255, 255) then it is background, otherwise, it is seed kernel.

In the present example embodiment of the invention, computer (240) is programmed to compute an average value for hue across the kernel area of the image that excludes the non-kernel portions of the image and any large light frequency discrepancies within the image. For example, once the above described pixel color balancing calibration adjustments are performed by computer (240) for the seed/grain kernel area of an image, an average hue value, $H_{avg}$, may then be computed according to Equations 1 and 2 below as follows:

$$H_{avg} = \frac{\sum_{i=minpixel}^{maxpixel} X_i}{\text{number total pixels}} \qquad \text{EQU. 1}$$

where:

$$X = \cos^{-1}\left[\frac{\frac{1}{2}[(R-G)+(R-B)]}{[(R-G)^2+(R-B)(G-B)]^{\frac{1}{2}}}\right] \qquad \text{EQU. 2}$$

where:
R=red value of pixel
G=green value of pixel
B=blue value of pixel

Likewise, computer (240) is also programmed to determine an average value for saturation across the kernel area of the image that excludes the non-kernel portions of the image and any large light frequency discrepancies within the image. For example, once the pixel color balancing calibration adjustments are performed for a given seed/grain sample image kernel area, an average saturation value, $S_{avg}$, may then be computed according to Equations 3 and 4 below as follows:

$$S_{avg} = \frac{\sum_{i=minpixel}^{maxpixel} X_i}{\text{number total pixels}} \qquad \text{EQU. 3}$$

where:

$$X = 1 - \left[\frac{\min(R, G, B)}{\text{intensity}}\right] \qquad \text{EQU. 4}$$

where:
R=red value of pixel
G=green value of pixel
B=blue value of pixel
Intensity=computed intensity of the RGB values (as described below)

Similarly, computer (240) is also programmed to determine an average value for intensity across the kernel area of the image that excludes the non-kernel portions of the image and any large light frequency discrepancies within the image. For example, once the pixel color balancing calibration adjustments are performed by computer (240) for a given seed/grain sample image kernel area, an average intensity value, $I_{avg}$, may then be computed according to Equations 5 and 6 below as follows:

$$I_{avg} = \frac{\sum_{i=minpixel}^{maxpixel} X_i}{\text{number total pixels}} \qquad \text{EQU. 5}$$

where:

$$X = \frac{R+G+B}{3} \qquad \text{EQU. 6}$$

where:
R=red value of pixel
G=green value of pixel
B=blue value of pixel

Using computer (240), pixels corresponding to the kernel portions of a given seed/grain sample image are further analyzed and identified as corresponding to the hard endosperm (HE) portion of the kernel according to the relationship provided by Equation 7 below:

$$P_{HE} = I_p \geq AI*n \qquad \text{EQU. 7}$$

where:
$P_{HE}$ is a pixel corresponding to the hard endosperm (HE) portion of a seed/grain kernel;
$I_p$ is the pixel intensity value of the pixel being analyzed;
AI is the average intensity, $P_{avg}$, of all pixels identified as corresponding to the seed/grain kernel portions of an image; and
n is a predetermined equipment adjustment factor based on an equipment specific calibration—which may be computed, for example, by performing an optical analysis using the apparatus of the present invention on a seed/grain sample of known hard endosperm percentage, computing a hard endosperm percentage (as explained below) and developing a numerical value for the adjustment factor n that results in producing a computed hard endosperm percentage that is closest to the known hard endosperm percentage value. For example, a known standard test is performed by the Illinois Crop Improvement Association (ICIA).

In other words, if the intensity of a particular pixel is greater than or equal to the average pixel intensity multiplied by the predetermined equipment adjustment factor, n, then the pixel is considered as belonging to the hard endosperm portions of the image. One of ordinary computer programming skill will appreciate that computer system (240) may be readily programmed using conventional programming techniques to identify the hard endosperm pixels according to Equation 7 above. One of ordinary skill will also appreciate that equipment adjustment factor "n" may vary for seed/grain samples of different kernel colors such as, for example, yellow and white corn due to the inherent transparency qualities of the particular sample and the particular type of white light source used for backlight (207).

The percent of hard endosperm present in a particular image of a seed/grain sample image may be determined by programming computer (240) to keep track of the total number of pixels corresponding to the kernel portions of a back-lit color adjusted image of the sample (i.e., excluding the non-kernel portions) and then counting and computing the percentage of pixels that are identified as corresponding to the hard endosperm portions. For example, one of ordinary computer programming skill will appreciate that computer system (240) may be programmed, using known conventional programming techniques, to compute a hard endosperm percentage, HE %, based upon a total count of pixels comprising the kernel area in an acquired image and a count of pixels identified as hard endosperm according to Equation 7 and then compute a hard endosperm percentage using Equation 8 below as follows:

$$HE\% = (hec/tc) * 100 \qquad \text{EQU. 8}$$

where:
HE %=percent hard endosperm
hec=total count of pixels identified as hard endosperm
tc=total count of pixels comprising kernel area of image In an embodiment of the present invention, top/bottom combined images of seed/grain sample (205) are acquired using digital camera (255). The hard endosperm portions of the seed/grain sample are identified using pixel data from an acquired back-lit image, while seed/grain color traits are determined from the separately acquired top/bottom combined image. In identifying the hard endosperm portions and determining hard endosperm percent, only pixel data acquired from the back-lit image of a seed/grain sample is used. Pixel intensity RGB values are obtained, an average pixel intensity is computed using Equations 5 and 6 above, and the percentage of pixels corresponding to hard endosperm portions are identified and computed using Equations 7 and 8 above. Preferably, the separately acquired top/bottom combined image of the sample is used for determining the color traits of the seed/grain sample. (Pixel intensity RGB values and average pixel intensity determined from the acquired top/bottom combined image of the seed/grain sample are typically different and more useful for producing an accurate color trait analysis than pixel values determined from the back-lit image.) Pixels corresponding to soft endosperm and embryo portions of the sample (identified from the back-lit image) are removed from the acquired top/bottom combined image of the sample. Color traits of the seed/grain sample are then uniquely identified by computing the average hue, average saturation and average intensity values (e.g., using Equations 1-6 above) for all the pixels remaining, which correspond to the hard endosperm portions of the top/bottom combined image. Color/whiteness traits estimated from the hard endosperm portion of the grain are more useful than whole kernel estimates, because they are not confounded with embryo color and size, nor grain texture. Furthermore, it is preferable to make color/whiteness estimates from top/bottom combined images, rather than top-lit images, because the former is influenced by the color of the endosperm as well as that of the external layers of the seed/grain.

Table 1 below shows numerical results of an example analysis of fourteen different corn seed samples (A-N) obtained using the method and apparatus of the embodiment shown in FIG. 3. The first eight samples (A-H) are yellow corn, and the remaining samples (I-N) are white corn. For each sample, the table lists the relative kernel area, hard endosperm (HE) area and computed percentage of hard endosperm (HE Pct) based on pixel information from an acquired back-lit image and the average color saturation, intensity and hue of pixels based on information from an acquired top-lit image. The table also lists the average color saturation (whiteness), hue (color) and intensity of each sample, obtained from top/bottom combined images, using only pixels in the hard endosperm portion of the seed/grain. In this example, each sample consists of the same number of seeds, areas are relative expressed in pixels, and hard endosperm values were computed using an equipment adjustment factor "n" of 0.75.

TABLE 1

| Sample | Kernel Area | HE Area | HE Pct | Saturation | Intensity | Hue |
|---|---|---|---|---|---|---|
| A | 29215 | 18085 | 0.62 | 0.39 | 177.14 | 32.68 |
| B | 26831 | 16322 | 0.61 | 0.39 | 164.33 | 27.45 |
| C | 27902 | 14290 | 0.51 | 0.33 | 179.15 | 32.63 |
| D | 25085 | 17591 | 0.7 | 0.46 | 165.77 | 29.39 |
| E | 20523 | 13147 | 0.64 | 0.39 | 176.69 | 33.42 |
| F | 26529 | 17847 | 0.67 | 0.42 | 176.08 | 34.83 |
| G | 31479 | 14966 | 0.48 | 0.26 | 182.75 | 30.67 |
| H | 30924 | 18239 | 0.59 | 0.42 | 171.12 | 31.99 |
| I | 31097 | 18443 | 0.59 | 0.18 | 201.95 | 35.94 |
| J | 27553 | 19470 | 0.71 | 0.14 | 209.75 | 33.77 |
| K | 27896 | 18525 | 0.66 | 0.09 | 217.03 | 34.71 |
| L | 25731 | 15413 | 0.6 | 0.09 | 213.6 | 35.34 |
| M | 20979 | 15538 | 0.74 | 0.12 | 212.28 | 33.53 |
| N | 26349 | 18229 | 0.69 | 0.17 | 198.67 | 33.91 |

FIG. 4 depicts on the left a back-lit image and on the right a top/bottom lit FIG. 2 embodiment combined images of the 15 corn seeds in a separate sample. In FIG. 4 the computer is displaying the images captured by the camera. The left back lit only picture shows the translucent lighter portion of the seed that corresponds to the hard endosperm. The picture on the right clearly shows the top/bottom lit seed including the embryo portion in the center of the seed.

Figure 5:
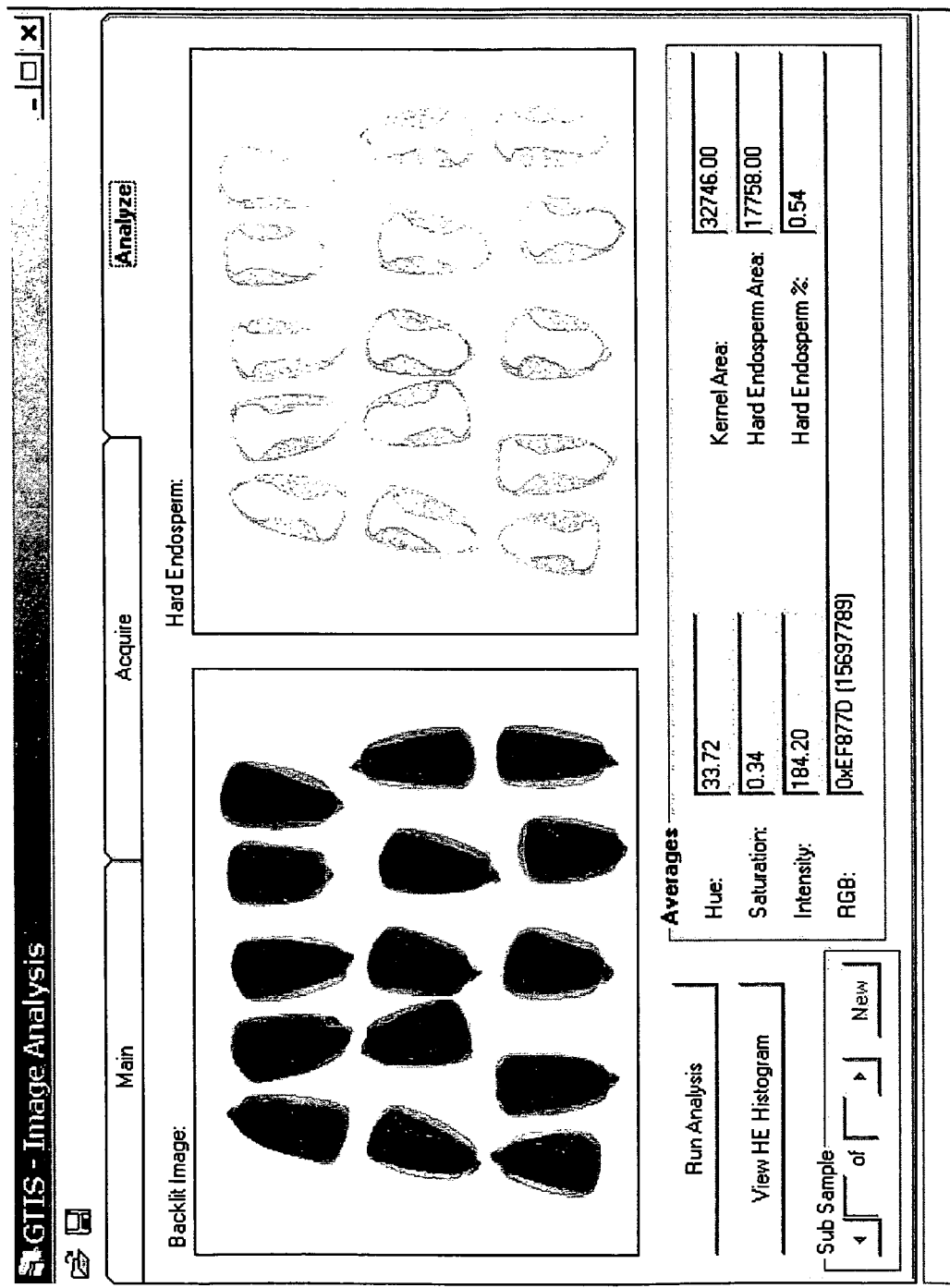
FIG. 5 shows the analysis graphics and results of hue, saturation, intensity, RGB, kernel area, hard endosperm area and hard endosperm % performed by the computer based on the back-lit and top-lit/backlit images of a corn seed/grain sample produced in accordance with the present invention in FIG. 2.

As shown in the captured image on FIG. 4 in the left picture, the seeds/grain on the stage are placed with the embryo-side facing upwards. When seed/grain are in this arrangement, the accuracy of the optical analysis using the present invention is optimized. This is particularly true in grain that has the embryo much more visible on one side of the grain than on the other side of the grain. Turning to FIG. 5 we again see the same image as is shown on the left of FIG. 4. The images on the left side of both FIGS. 4 and 5 are back-lit images, and the image on the right of FIG. 5 is the hard endosperm portions of the corresponding top/bottom combined images. The right image of FIG. 5 shows the image of the hard endosperm alone with all other portions of the seed being shown as white. This image on the right is employed in the hue, saturation and intensity calculations which are displayed below the two images. The visual comparison of the two images shows that only the translucent portion of the backlit image is visible in the analyzed image. The traits analyzed are shown below the two images. The analysis was run by the computer using an equipment adjustment factor of 0.69. This factor adjusts the intensity of the light on the image.

Figure 7A:
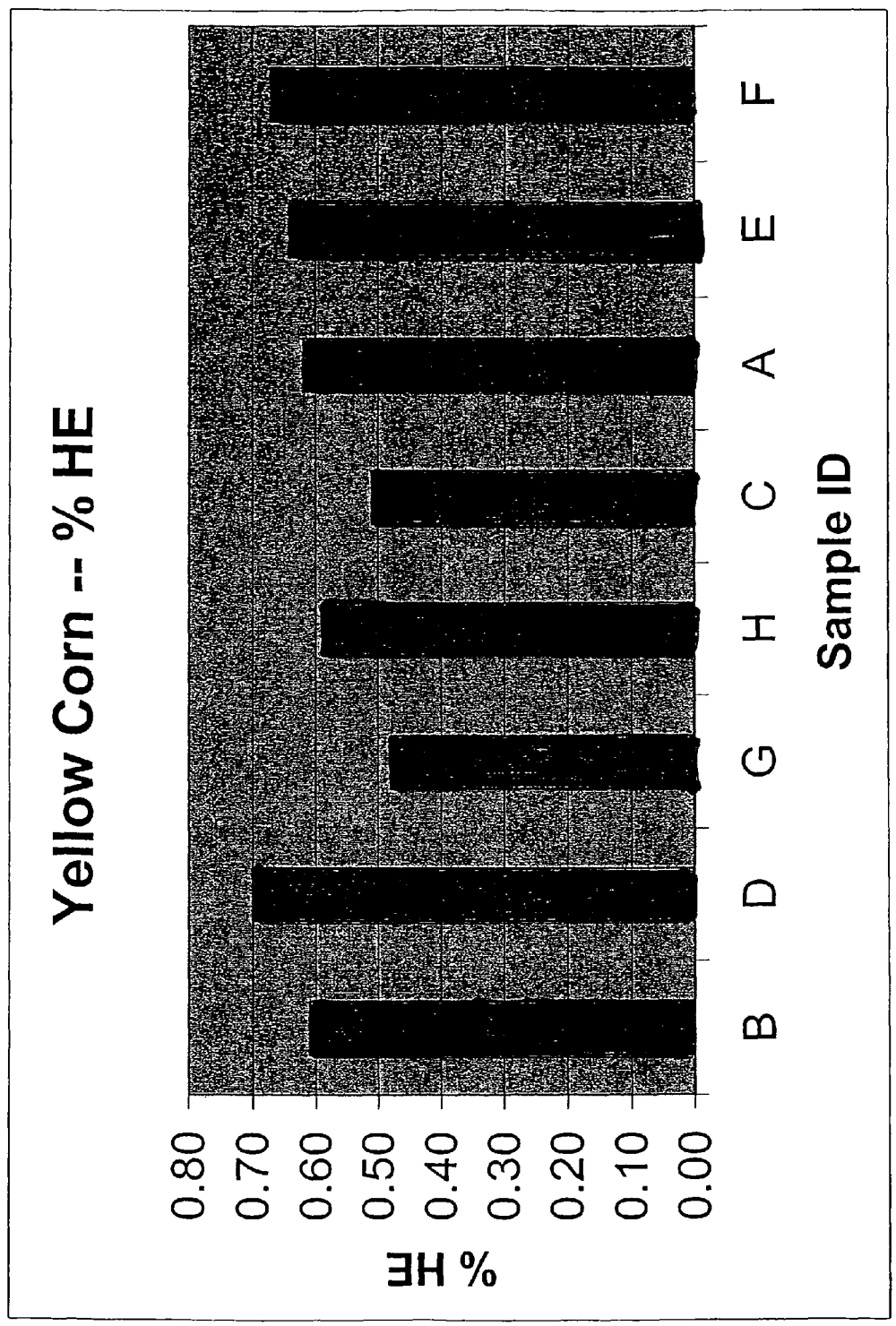
FIGS. 7A-F are results produced from Table 1 and gathered from the embodiment of FIG. 3.
Figure 7B:
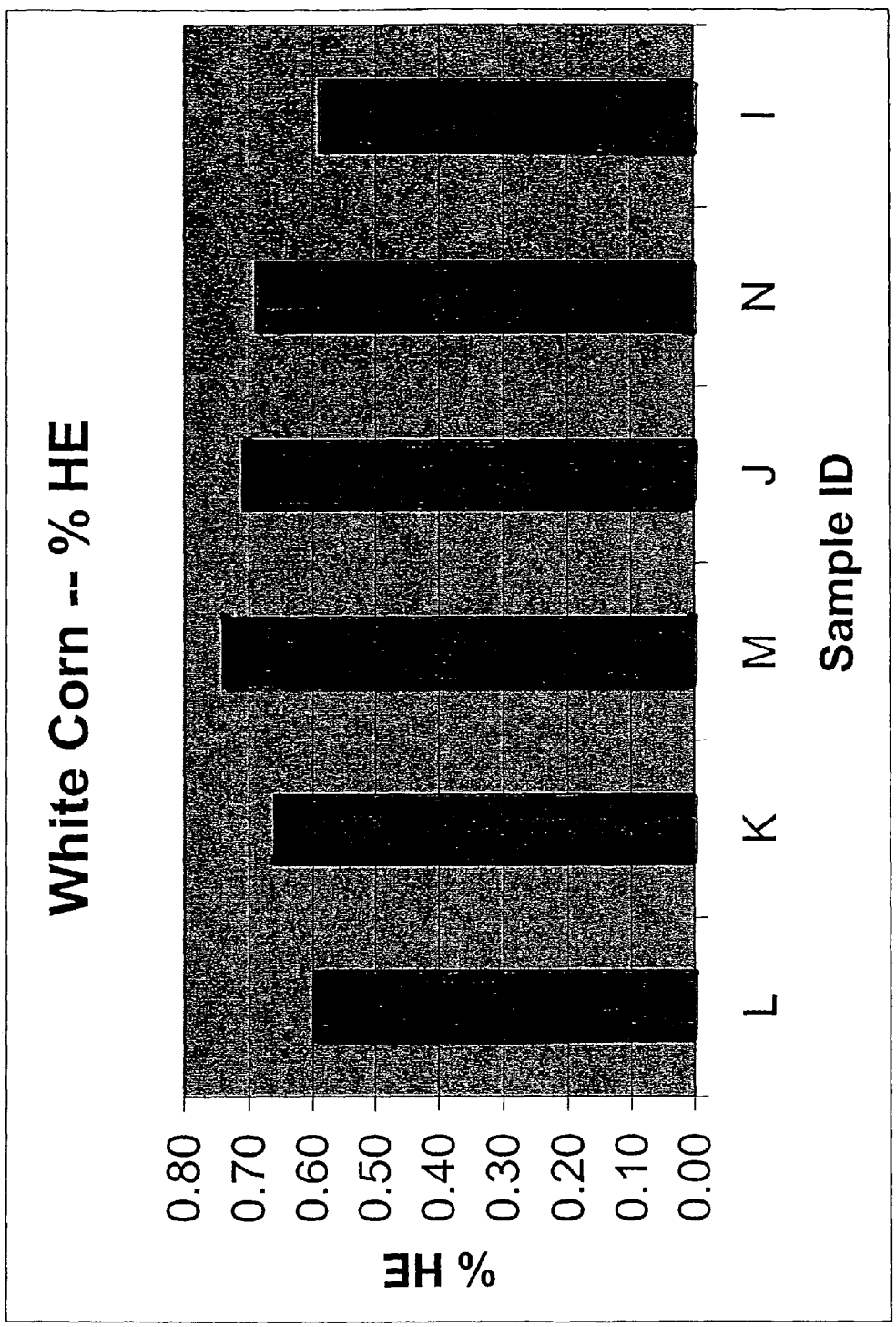
Figure 7C:
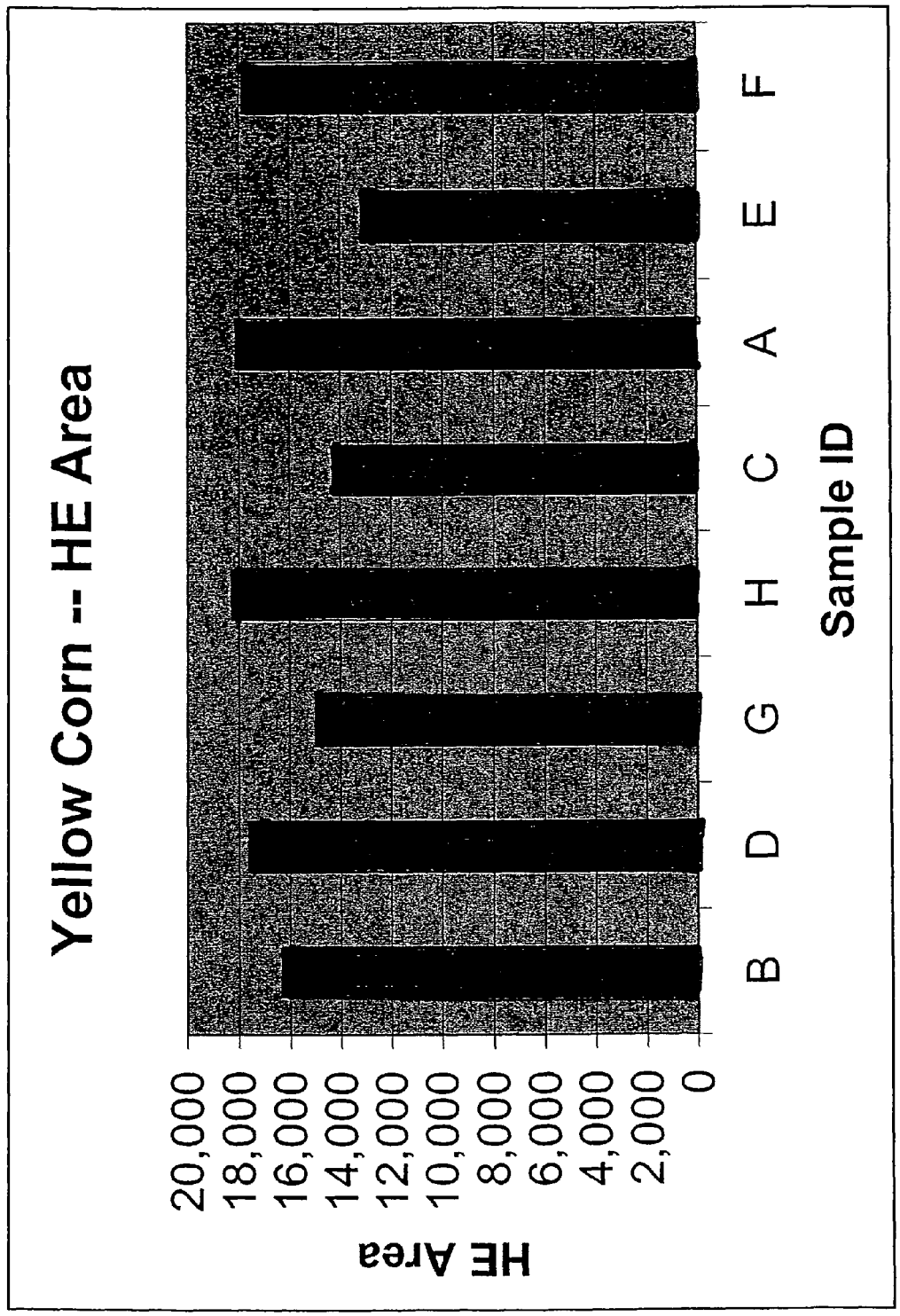
Figure 7D:
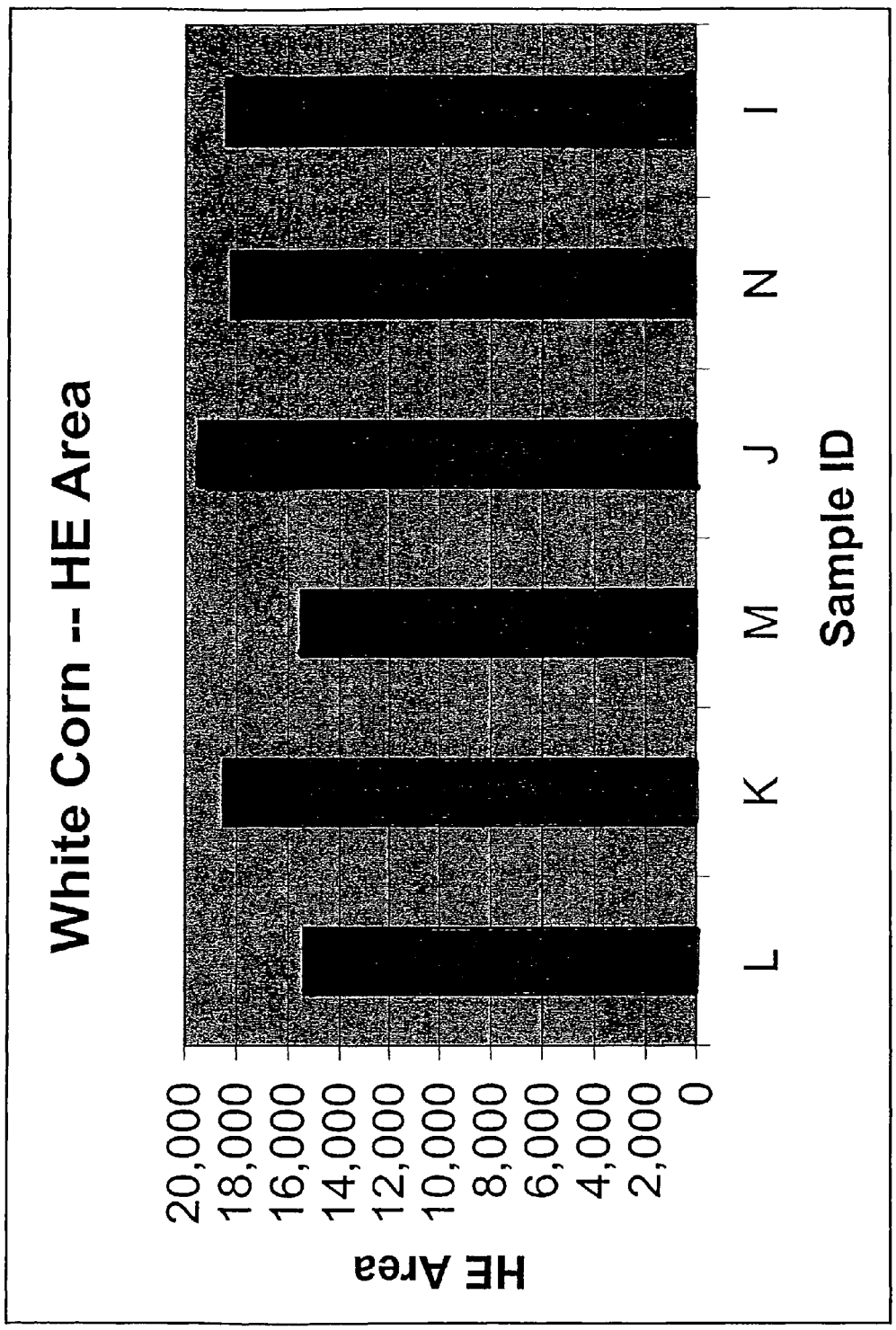
Figure 7E:
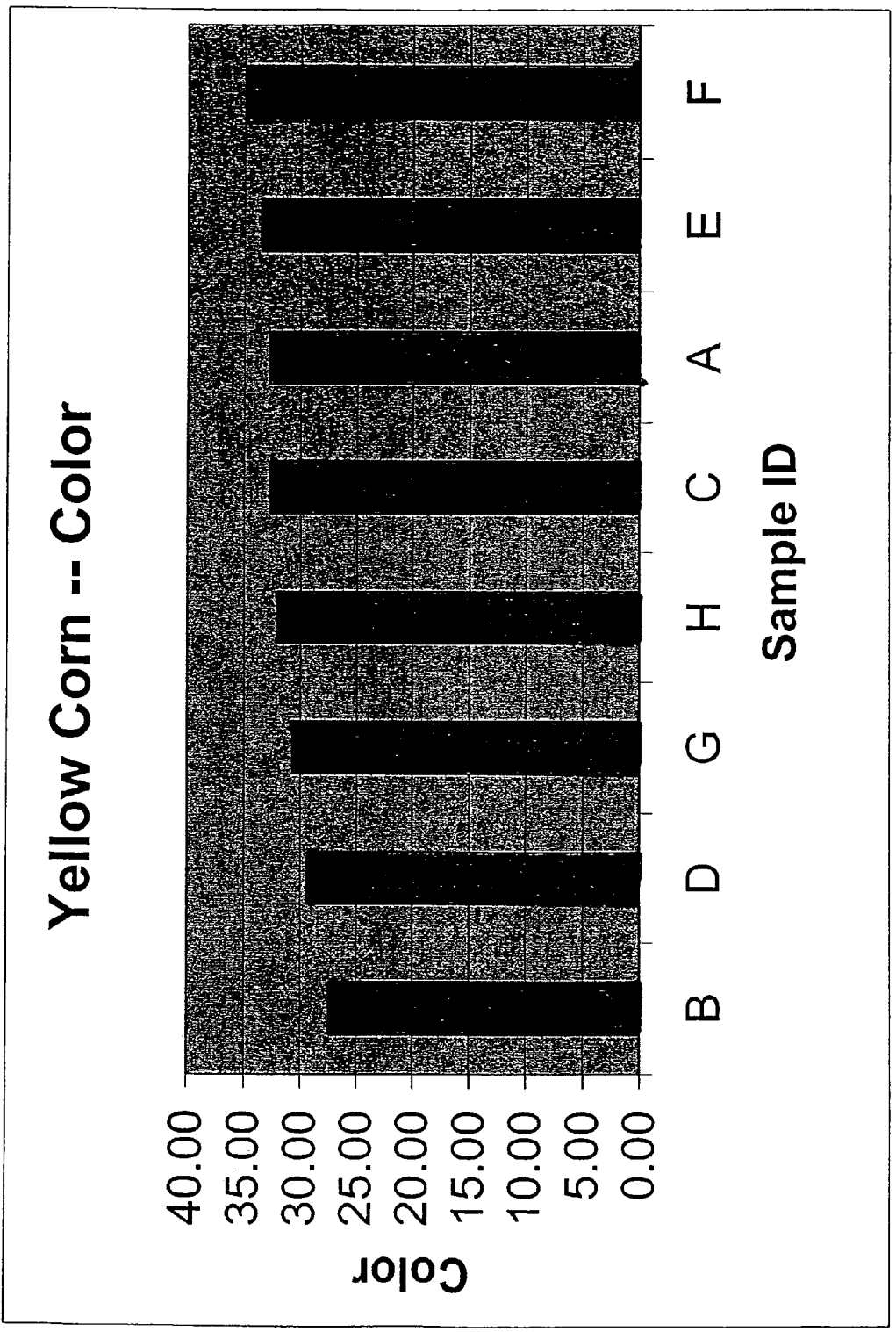
Figure 7F:
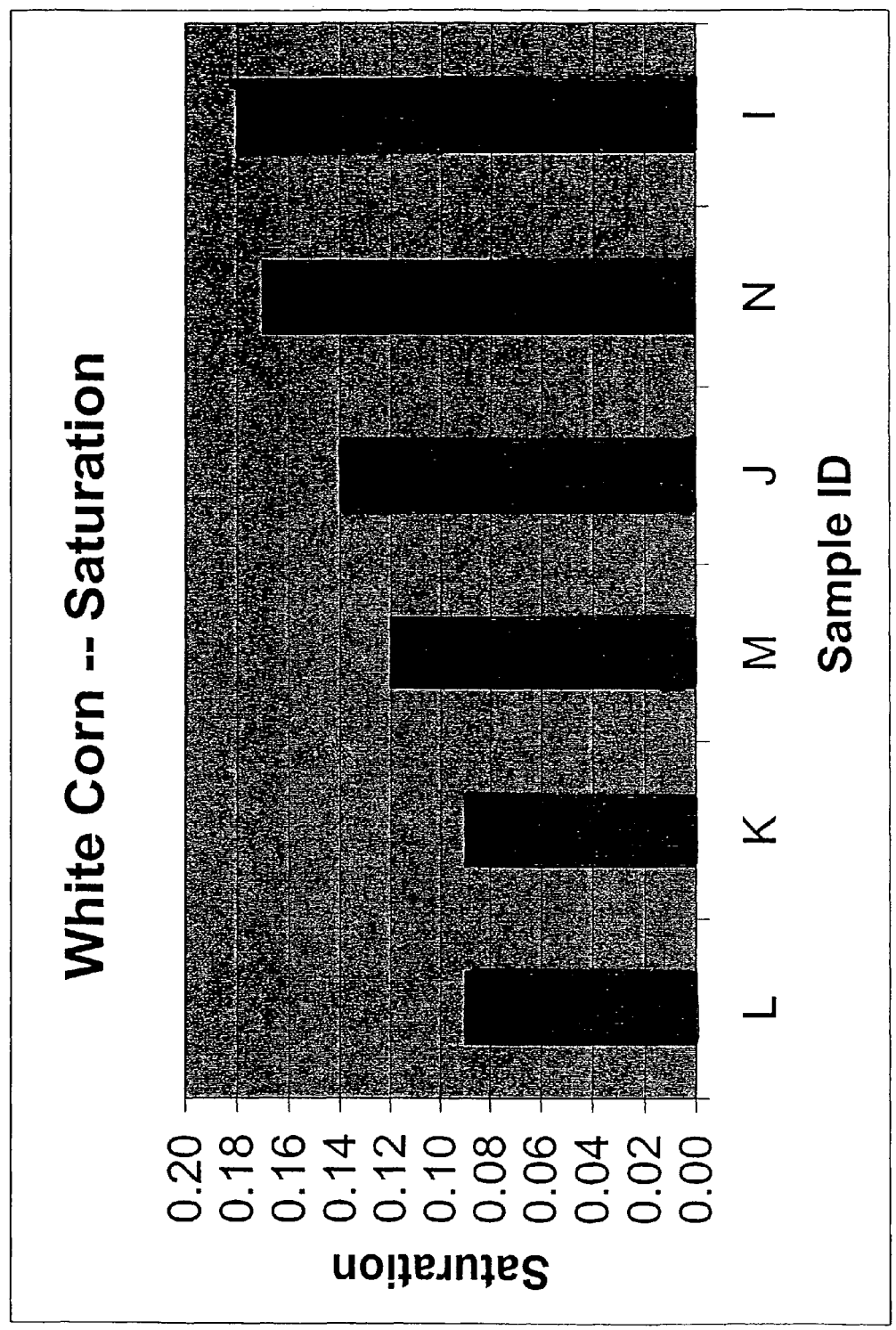

Each of the samples, designated in Table 1, had an acquired image and an analyzed image such as shown in FIGS. 4 and 5. The data from the computer analysis results listed in Table 1 is displayed in graphical form in FIGS. 7A-7F, with samples ordered in increasing hue (yellow corn) or saturation (white corn). Percent hard endosperm (as a percent of kernel area) for the yellow and white samples are shown in FIGS. 7A and 7B, respectively. The values for hard endosperm area are summarized in FIGS. 7C and 7D. Color (hue) of the yellow corn samples is presented in FIG. 7E, while whiteness (saturation) of the white corn samples can be found in FIG. 7F. Hue is an indication of relative color, with lower values being more reddish and higher values more yellowish. Saturation is an indication of the absence of color, with lower values being a "cleaner" white.

Since the method and apparatus of the present invention as described herein is not destructive of seeds/grains being analyzed, the present invention may be used for selecting traits of the seeds/grains from a breeding population. The present invention may also be used to quantify grain samples of experimental or commercial hybrids or varieties of corn or other crops to determine suitability for various milling applications. Moreover, the present invention may be used and employed not only when the seed/grain is from a commercial hybrid, but also during the breeding and research process of developing a commercial hybrid having the desired seed/grain traits. The seeds may be analyzed for HE %, color, etc, as described herein, and the results of the analysis may be used in breeding for complementary traits. The present invention may also be used to determine the kernel area of, an individual seed/grain or, for example, by using a predetermined number of kernels per sample, an average kernel size may be computed. When the number of kernels is the same in all samples, the hard endosperm area (HE area) can be used to reasonably predict dry milling yield of large grit components.

While the present invention has been described it is to be understood that the invention is not to be limited to the disclosed embodiment, but on the contrary, is intended to cover various modifications and equivalent arrangements included within the spirit and scope of the appended claims.

What is claimed is:

1. A method of optically analyzing seed and/or grain quality, comprising:
    a) acquiring an image of a seed/grain sample from an illuminated area of a stage, a first light source positioned to project light through said stage which supports the sample, the first light being of sufficient intensity such that at least some light passes through both the stage and the sample, the illuminated area is illuminated with said light source wherein said light source comprises non-polarized visible halogen illumination, said image comprising a seed/grain sample, the image comprising a plurality of pixels wherein each pixel has at least an associated Red (R), Green (G), and Blue (B) color value;
    b) acquiring said image of said sample with a camera, said camera positioned to capture light from said first light source and from a second light source which light has either passed through the sample or has reflected from said sample in combination with a flash of xenon light to compensate for inconsistencies in pixel intensity ranges across said acquired image,
    c) identifying a subset of pixels in said image that correspond to seed/grain areas of said image, said grain pixels,
    d) identifying another subset of pixels that correspond to hard endosperm portions of the seed/grain sample, said hard endosperm pixels; and,
    e) analyzing pixels selected from the group consisting of: the plurality of pixels, the grain pixels and the hard endosperm pixels to assert the seed/grain quality, wherein said seed/grain color quality is analyzed based on the hard endosperm pixels.

2. The method of claim 1 further comprising:
    determining a value indicative of a percentage of pixels identified as grain pixels that also correspond to hard endosperm pixels.

3. The method of claim 1 wherein said plurality of pixels and the grain pixels or the hard endosperm pixels are acquired using the first light source.

4. The method of claim 1 wherein said illuminated area of the stage supporting the sample is translucent.

5. The method of claim 1 wherein said first light source is positioned to project light such that the sample is backlit.

6. The method of claim 1 wherein a second light source is positioned to project light wherein the sample is frontlit.

7. The method of claim 1 wherein said stage has a first surface and an opposite second surface, and wherein light from a second light source initially projects through the second surface of the stage and said light from said first light source initially projects through the first surface of the stage wherein the sample is both backlit and frontlit.

8. The method according to claim 7 further comprising the step of: determining color traits of the sample by computing one or more of average hue, average saturation or average intensity of said hard endosperm pixels.

9. The method of claim 1 further comprising: a camera positioned to capture light from said first light source which has passed through both the stage surface and the sample.

10. The method of claim 1, wherein a pixel R, G, B color value corresponds to a predetermined white color.

11. The method of claim 1, wherein a pixel from the plurality of pixels of said image is identified as a pixel within the subset of pixels corresponding to grain pixels if said pixel has R, G and B color values that are not equivalent to a white color.

12. The method of claim 1, wherein a pixel from the plurality of pixels corresponds to grain pixel subset if said pixel has R, G and B color values are not the predetermined white.

13. The method of claim 1, wherein pixels corresponding to hard endosperm pixels are identified as pixels having an intensity value that is greater-than or equal-to an average grain pixel intensity multiplied by a predetermined equipment adjustment factor.

14. The method of claim 1, wherein a pixel of said image is identified as corresponding to a hard endosperm subset, $P_{HE}$, of the seed/grain sample in accordance with the following relationship:

$$P_{HE} = I_p \geq AI*n$$

where:
    $I_p$ is the pixel intensity value of a pixel of said image;
    AI is an average intensity, $I_{avg}$, of pixels identified as corresponding to said grain pixels; and
    n is a predetermined calibration factor associated with an apparatus used to acquire an image of the seed/grain sample.

15. The method of claim 1, wherein a hard endosperm percentage, HE %, is determined based on pixels comprising kernel areas of the grain pixels and pixels identified as hard endosperm pixels, according to the following relationship:

$$HE\% = (hec/tc)*100$$

where:
    HE %=percent hard endosperm
    hec=number of pixels identified as hard endosperm
    tc=number of pixels comprising kernel areas of the grain pixels.

16. The method of claim 1, wherein there are a plurality of samples analyzed and wherein a number of kernels in each of said samples is kept constant, throughout said plurality of said samples, and hard endosperm area, HE Area, is determined, being equal to the number of pixels identified as hard endosperm (hec) for each respective sample.

17. The method of claim 16, wherein the HE Area of each respective sample can be compared to determine the sample with the most HE Area.

18. A method of breeding corn comprising the steps of:
    analyzing corn seed by the method of claim 1 and selecting corn seed with at least one desirable quality comprising hard endosperm area, hard endosperm percent, hue, or saturation;
    growing said selected corn seed into a plant and then breeding with said plant and producing seed thereon; and
    analyzing said seed for at least one desirable quality trait.

19. The method of claim 18 wherein said breeding is either inbreeding or cross-breeding.

20. A apparatus for optically analyzing a seed and/or grain sample, comprising:
- a stage having at least one surface used for supporting a seed/grain sample, said surface being at least partially translucent;
- a first light source wherein said illumination is visible halogen light which is not polarized light and not fluorescent light positioned proximate the stage, on an opposite side of the surface supporting the sample, the first light source providing substantially uniform illumination over the stage surface supporting the sample and said light source providing light of sufficient intensity such that at least some light passes through both the stage surface and the sample;
- a second light source positioned above a surface supporting the sample, the second light source providing substantially uniform illumination over the stage surface supporting the sample;
- a camera positioned to capture light from said first light source and said second light source and a xenon light flash, which light has either passed through the sample or has reflected from said sample and,
- a computer engaged with said camera, to analyze the captured image of the seed/grain sample.

21. The apparatus of claim 20 wherein said first and second light sources produce visible light.

* * * * *